United States Patent
Zheng et al.

(10) Patent No.: US 12,056,872 B2
(45) Date of Patent: Aug. 6, 2024

(54) METHOD FOR EXTRACTING SIGNIFICANT TEXTURE FEATURES OF B-ULTRASONIC IMAGE AND APPLICATION THEREOF

(71) Applicant: Zhejiang University, Zhejiang (CN)

(72) Inventors: Min Zheng, Zhejiang (CN); Dongsheng Ruan, Zhejiang (CN); Nenggan Zheng, Zhejiang (CN); Yu Shi, Zhejiang (CN); Linfeng Jin, Zhejiang (CN)

(73) Assignee: Zhejiang University, Hangzhou (CN)

( * ) Notice: Subject to any disclaimer, the term of this patent is extended or adjusted under 35 U.S.C. 154(b) by 416 days.

(21) Appl. No.: 17/398,142

(22) Filed: Aug. 10, 2021

(65) Prior Publication Data
US 2021/0374956 A1    Dec. 2, 2021

Related U.S. Application Data

(63) Continuation of application No. PCT/CN2020/099590, filed on Jun. 30, 2020.

(30) Foreign Application Priority Data

May 31, 2020    (CN) .......................... 202010487055.5

(51) Int. Cl.
| | |
|---|---|
| G06T 7/00 | (2017.01) |
| A61B 8/08 | (2006.01) |
| G06T 7/40 | (2017.01) |
| G16H 50/20 | (2018.01) |

(52) U.S. Cl.
CPC .............. *G06T 7/0012* (2013.01); *A61B 8/08* (2013.01); *A61B 8/5223* (2013.01); *A61B 8/5292* (2013.01); *G06T 7/40* (2013.01); *G16H 50/20* (2018.01); *G06T 2207/10132* (2013.01); *G06T 2207/20021* (2013.01); *G06T 2207/20081* (2013.01); *G06T 2207/30024* (2013.01); *G06T 2207/30056* (2013.01)

(58) Field of Classification Search
CPC ......... A61B 8/08; A61B 8/085; A61B 8/5223; A61B 8/5292; G06T 2207/10132; G06T 2207/20021; G06T 2207/20081; G06T 2207/20084; G06T 2207/30024; G06T 2207/30056; G06T 7/0012; G06T 7/40; G16H 30/40; G16H 50/20
See application file for complete search history.

(56) References Cited

FOREIGN PATENT DOCUMENTS

CN    103169506 A    6/2013

*Primary Examiner* — Amelie R Davis

(57) ABSTRACT

A method for extracting significant texture features of a B-ultrasonic image and application thereof discloses a channel attention mechanism network, i.e. a context activation residual network, which is designed to effectively model the B-ultrasonic liver fibrosis texture information, and which uses the global context information to strengthen important texture features and suppress useless texture features, such that the deep residual network can capture more significant texture information in the B-ultrasonic images. The process can be mainly divided into two phases: training and testing. During the training phase, the context activation residual network may be trained by using the B-ultrasonic image blocks as input and the pathological results of liver biopsy as labels. During the testing phase, the B-ultrasonic image blocks may be input into the trained non-invasive liver fibrosis diagnosis model to obtain the liver fibrosis staging result for each ultrasonic image.

6 Claims, 3 Drawing Sheets

METHOD FOR EXTRACTING SIGNIFICANT TEXTURE FEATURES OF B-ULTRASONIC IMAGE AND APPLICATION THEREOF

CROSS REFERENCE TO RELATED APPLICATIONS

The present application is a Continuation Application of PCT Application No. PCT/CN2020/099590 filed on Jun. 30, 2020, which claims the benefit of Chinese Patent Application No. 202010487055.5 filed on May 31, 2020. All the above are hereby incorporated by reference in their entirety.

FIELD OF THE INVENTION

The invention pertains to the technical field of B-ultrasonic diagnosis, and specifically relates to a method for extracting significant texture features of a B-ultrasonic image and application thereof, in particular to a method for non-invasive B-ultrasonic diagnosis of liver fibrosis based on a context activation residual network.

BACKGROUND OF THE INVENTION

Liver fibrosis is a key stage in the development of various chronic liver diseases to cirrhosis and an important link that affects the prognosis of chronic liver diseases. In clinical diagnosis, liver biopsy is regarded as gold standard for diagnosing liver fibrosis. However, such an approach may incur serious traumatic problems and could be not well tolerated by many patients. In recent years, domestic and foreign scholars have devoted themselves to study for non-invasive diagnosis methods for liver fibrosis. Ultrasonic imaging diagnosis has been widely used in the diagnosis of liver fibrosis due to its safety, cost benefit, non-invasiveness, real-time and other advantages. However, limited by the quality of ultrasonic imaging, the diagnostic accuracy of liver fibrosis by ultrasound is highly dependent on the doctor's clinical diagnosis experience. In order to solve this problem, it is particularly important to develop an objective, accurate and intelligent computer-aided diagnosis method.

Currently, B-ultrasonic diagnostic methods of liver fibrosis based on computer-aided diagnosis may be mainly based on traditional machine learning methods or deep learning methods. The former generally uses one or more texture extraction algorithms, such as gray-level co-occurrence matrix and wavelet transform, to model the texture information of the liver parenchyma region in a B-ultrasonic image, and then use classifiers, such as support vector machines, to complete staging of liver fibrosis. Such methods often cannot be applied to large-scale data concentration and thus will not obtain accurate staging of liver fibrosis. The latter may use a convolutional neural network in deep learning to achieve end-to-end liver fibrosis staging. Compared with the former, the latter usually provided with better staging performance can be more easily trained and deserve further application. However, due to lack of additional supervision of such existing methods, the network cannot accurately extract the texture features of liver fibrosis in the B-ultrasonic image, resulting in a very low diagnosis rate and thus difficult to be applied to clinical diagnosis. Therefore, how to capture the most critical texture features in B-ultrasonic images simply and effectively is a key question in accurately diagnosing liver fibrosis.

SUMMARY OF THE INVENTION

In view of the technical problems in the prior art stated above, the present invention provides a method for extracting significant texture features of a B-ultrasonic image based on a context activation residual network for non-invasive B-ultrasonic diagnosis of liver fibrosis. The method designs a lightweight channel attention mechanism that can effectively capture the texture features of different liver fibrosis in B-ultrasonic images and obtain accurate staging of liver fibrosis.

A method for extracting significant texture features of a B-ultrasonic image based on a context activation residual network may include the following steps.

At step (1), multi-center ultrasonic image data sets may be established, which includes B-ultrasonic images of different patients and corresponding liver biopsy results.

At step (2), image blocks of three different resolutions may be cropped from each of the B-ultrasonic images (preferably, the resolutions are 60×60, 100×100 and 120×120, respectively, the number of the cropped blocks with each resolution being between 2 to 4), for data enhancement. The above-mentioned image block data sets may be partitioned into training sets and testing sets at a certain ratio (preferably, training sets: testing sets is 7:3), where the B-ultrasonic image block data is used as model input data, and the liver biopsy result is used as model label data.

At step (3), ImageNet® 2012 data sets may be used to perform transfer learning on a deep residual network based on the context activation residual network to obtain a pre-trained liver fibrosis staging model.

At step (4), the pre-trained liver fibrosis staging model may be fine-tuned with the B-ultrasonic image training sets obtained in step (2), and a resulting B-ultrasonic liver fibrosis staging model based on the context activation residual network may be obtained.

At step (5), the B-ultrasonic image testing sets obtained in step (2) may be input into the B-ultrasonic liver fibrosis staging model, so as to obtain the liver fibrosis staging results for the B-ultrasonic images in the testing sets.

According to the METAVIR scoring system in combination with clinical treatment experience, liver fibrosis may be classified into three stages: normal or mild liver fibrosis (S0-S1), moderate liver fibrosis (S2-S3) and liver cirrhosis (S4).

The deep residual network based on the context activation residual network may be formed by stacking multiple context activation residual blocks. The context activation residual block may consist of two parts: residual block and context activation block. The residual block may be used to extract texture features in the B-ultrasonic image, and each channel for the residual block is responsible for extracting texture information for different features. The context activation block is intended to strengthen important texture features in the residual block, while suppressing useless texture features therein, so that the residual block may be used to extract more significant texture features in the B-ultrasonic image. The functional expression of the context activation residual block is as follows:

$$y = f(x) + x = \text{ReLU}(F(BN(W_3 g(W_2 g(W_1 x))))) + x$$

$$g(\cdot) = \text{R}_e\text{LU}(BN(\cdot))$$

where x and y are the input and output of the residual block, respectively, BN($\cdot$) is a batch normalization operation, ReLU($\cdot$) is a rectified linear unit (ReLU), F($\cdot$) is a context activation block, $W_1$ and $W_3$ are both 1×1 convolutions, and $W_2$ is 3×3 convolution.

Context activation block F($\cdot$) mainly includes three operations: global context aggregation, group normalization, and context activation. To simplify, let o=F($\cdot$). Global context aggregation is intended to obtain global texture information, specifically to obtain channel characterization vectors $z=[z_1, z_2, \ldots, z_k, \ldots, z_C]$ by global average pooling operation:

$$Z_k = \frac{1}{H \times W} \sum_{i=1}^{W} \sum_{j=1}^{H} o_k(i, j)$$

where W and H are the width and length of the feature map, C represents the number of channels in the feature map, $k \in \{1, 2, \ldots, C\}$. Group normalization is intended to eliminate inconsistent distribution of texture features caused by different samples and enhance robustness of the model. Specifically, the channel characterization vectors z are grouped by channel dimension, and then the feature vectors in each group are normalized, to obtain normalized channel characterization vectors $v=[v^1, \ldots, v^i, \ldots, v^G]$, where $v^i$ may be expressed as:

$$v^i = \frac{1}{\sigma^i}(p^i - \mu^i),$$

$$\mu^i = \frac{1}{m}\sum_{n \in S_i} Z_n, \sigma^1 = \sqrt{\frac{1}{m}\sum_{n \in S_i}(Z_n - \mu^1)^2 + \epsilon},$$

where $p^i=[z_{mi+1}, \ldots, z_{m(i+1)}]$, $$m = \frac{C}{G},$$

G represents the number of groups, $S_i$ represents the channel index set of the i-th group, $\in$ is a small constant for ensuring stable numerical calculation. Context activation is intended to learn the importance weight for each of the channels with global context information. The importance weight describes the importance of the texture feature learned by each of the channels. The higher the value, the more important the texture feature. Specifically, the process includes the step of performing a simple linear transformation on each of the channels and normalizing it to a value between 0 to 1 by a sigmoid function δ, as follows:

$a=\delta(\beta \cdot v+\gamma)$, where β and γ are learnable weights and biases, and · indicates that the corresponding channels are multiplied. The input may be readjusted by using the learned texture importance weight, and the output of the context activation block may be expressed as $\tilde{o}=o \cdot a$. Finally, the context activation block may be embedded into the residual block, and the output of the residual block may be re-expressed as:

$y=\text{ReLU}(\tilde{o})+x$.

Specifically, the process of pre-training the non-invasive diagnosis model of liver fibrosis by using ImageNet® in step (3) may further include the following steps.

The training sets in the ImageNet® data sets may be used for training the non-invasive liver fibrosis diagnosis model, wherein the input is natural image, and the label indicates the category of each image. The cross-entropy between the output value of the non-invasive liver fibrosis diagnosis model and the label may be used as the objective function, and the weight in the model may be continuously calculated and updated by a back-propagation algorithm and a gradient descent method until the value of the objective function is less than a set value or the total number of times of training is reached. Thereby, the pre-training of the non-invasive liver fibrosis diagnosis model is completed.

Specifically, the process of fine-tuning the non-invasive B-ultrasonic liver fibrosis diagnosis model in step (4) may further include the following steps.

Depending on the training sets obtained in step (2), the B-ultrasonic image blocks with different resolutions may be uniformly adjusted to have a resolution of 120×120, which is used as the input for the pre-trained non-invasive B-ultrasonic liver fibrosis diagnosis model. The size of the last output layer in the non-invasive B-ultrasonic liver fibrosis diagnosis model may be changed from 1000 to 3, and the pathological results of liver biopsy may be used as labels. Also, the cross-entropy between the output value of the non-invasive liver fibrosis diagnosis model and the label may be used as the objective function, and the weights in the model may be fine-tuned by a back-propagation algorithm and a gradient descent method until the value of the objective function is less than a set threshold or a total number of times of training is reached, so as to obtain the non-invasive B-ultrasonic liver fibrosis diagnosis model based on the context activation residual network.

Specifically, the process of obtaining the liver fibrosis staging results of the testing sets in step (5) may further include the following steps.

Depending on the testing sets obtained in step (2), the B-ultrasonic image blocks with different resolutions may be uniformly adjusted to have a resolution of 140×140, the central regions of the image blocks being cropped at a resolution of 120×120, which may be input into the fine-tuned non-invasive B-ultrasonic liver fibrosis diagnosis model. Then, the category corresponding to the largest value in the output vectors may be taken as the final liver fibrosis staging result of the B-ultrasonic image.

In addition, the present invention further provides a method for non-invasive B-ultrasonic diagnosis of liver fibrosis based on a context activation residual network, a medical device using the method for extracting significant texture features of a B-ultrasonic image, and its application in the non-invasive diagnosis of liver fibrosis.

The present invention introduces a novel attention mechanism network that proposes a channel attention module, i.e., context activation residual block, which can utilize global context feature information to learn the importance degree of the texture feature of each channel in the network features, in order to strengthen important texture features but suppress useless texture features and noise, thereby effectively improving the network's ability to model the B-ultrasonic image textures.

The context activation residual network is formed by stacking multiple context activation residual blocks. The context activation residual network is designed to effectively model the B-ultrasonic liver fibrosis texture information. Such a network uses the global context information to strengthen important texture features and suppress useless texture features, such that the deep residual network can capture more significant texture information in the B-ultrasonic images. The process can be divided into two phases: training and testing. During the training phase, the context activation residual network may be trained by using the B-ultrasonic image blocks as input and the pathological results of liver biopsy as labels. During the testing phase, the B-ultrasonic image blocks may be input into the trained non-invasive liver fibrosis diagnosis model to obtain the liver fibrosis staging result for each ultrasonic image. According to the invention, the liver fibrosis staging for the B-ultrasonic image can be rapidly and accurately estimated from the perspective of data driving.

DETAILED DESCRIPTION OF THE EMBODIMENTS

In order to describe the present invention in more detail, the technical solution of the present invention will be described in detail below with reference to the accompanying drawings and specific embodiments.

It is provided a method for non-invasive B-ultrasonic diagnosis of liver fibrosis based on a context activation residual network, which includes the following steps.

At step S1, multi-center ultrasonic image data sets are established, which include B-ultrasonic images and pathological results of liver biopsy. According to the METAVIR scoring system in combination with clinical treatment experience, liver fibrosis may be classified into three stages: normal or mild liver fibrosis (S0-S1), moderate liver fibrosis (S2-S3) and liver cirrhosis (S4). The pathological results of liver biopsy are used as labels and recorded as $l=[l_1, l_2, l_3]$.

At step S2, image blocks of three different resolutions are cropped from each of the B-ultrasonic images, the resolutions being 60×60, 100×100 and 120×120, respectively, and the number of the cropped blocks with each resolution being between 2 to 4. The obtained B-ultrasonic image blocks are partitioned into training sets and testing sets at a certain ratio (training sets: testing sets is 7:3).

Figure 1:
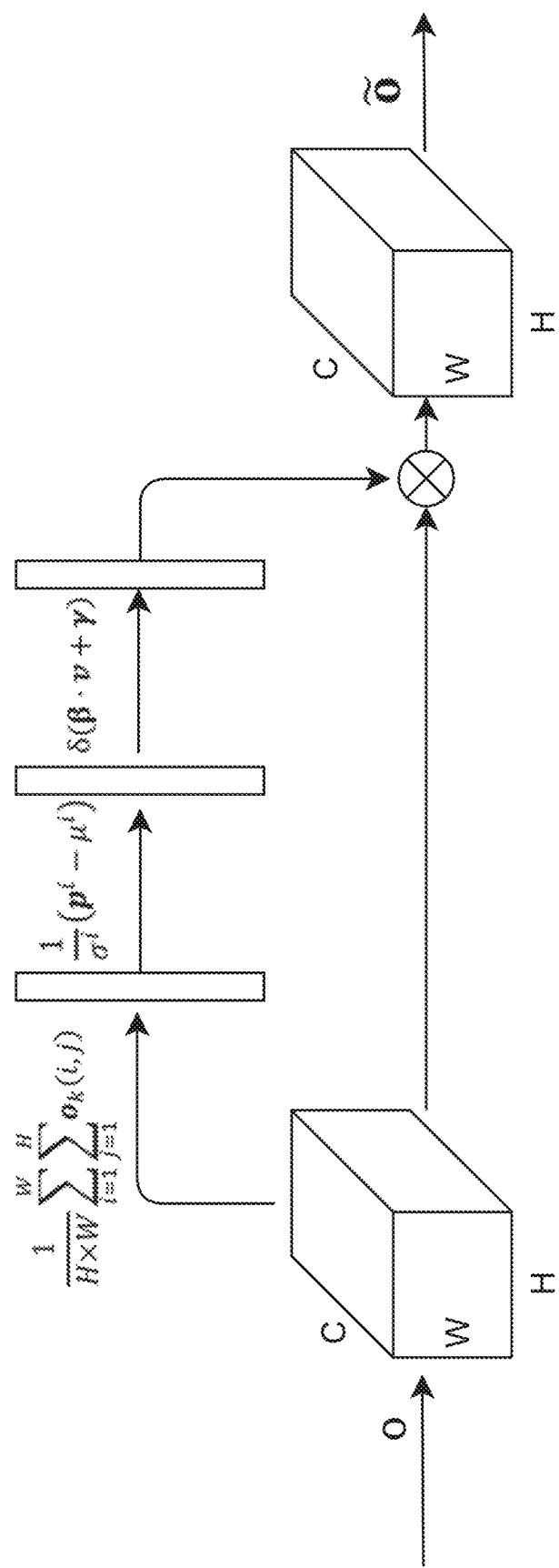
FIG. 1 is a diagram showing a context activation block.
Figure 2:
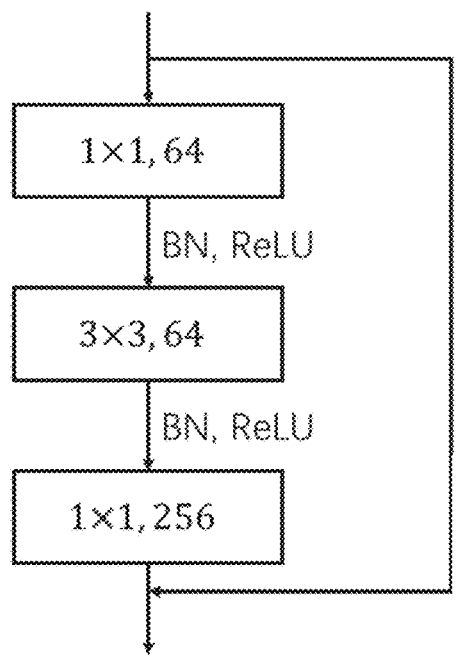
FIG. 2 is a diagram showing a residual block.
Figure 3:
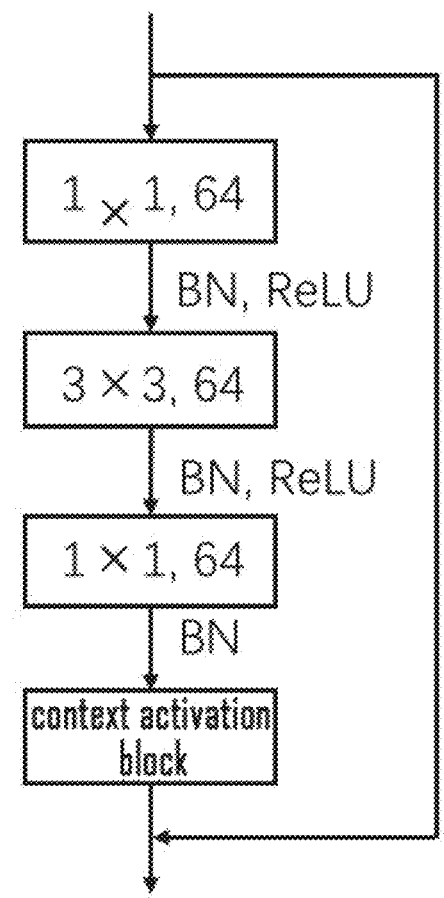
FIG. 3 is a diagram showing a context activation residual block.
Figure 4:
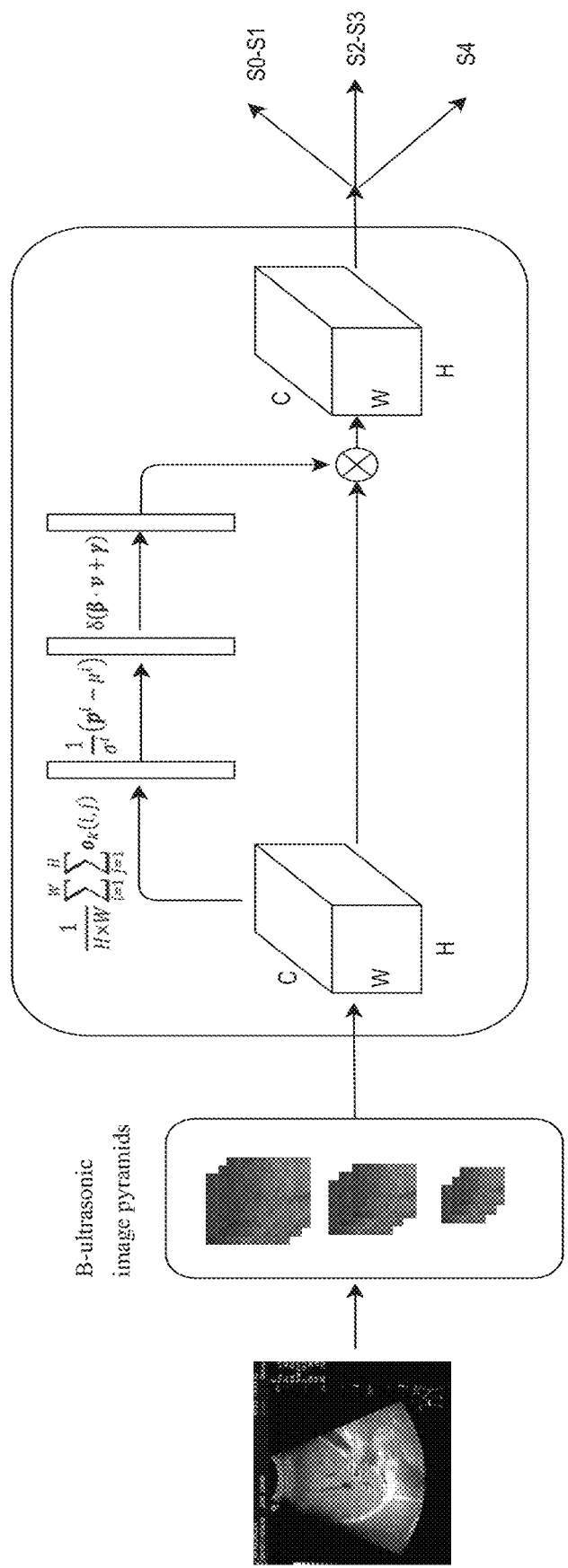
FIG. 4 is an overall frame view illustrating a method for extracting B-ultrasonic significant textures of liver fibrosis.

At step S3, the context activation block (FIG. 1) is embedded into the residual block (FIG. 2) to form a context activation residual block having its structure as shown in FIG. 3, wherein the network depth is set to d. A non-invasive B-ultrasonic liver fibrosis diagnosis model is established by simply stacking those residual blocks.

At step S4, ImageNet® data sets are used to pre-train the non-invasive B-ultrasonic liver fibrosis diagnosis model, and the weight parameters in the model are continuously updated by a back-propagation algorithm and a gradient descent method.

At step S5, the image blocks in the B-ultrasonic image training sets are uniformly adjusted to have a resolution of 120×120, which is used as the input for the non-invasive B-ultrasonic liver fibrosis diagnosis model, with the corresponding pathological results of liver biopsy as labels, and the weight parameters in the model are further updated by the back-propagation algorithm and the gradient descent algorithm.

At step S6, the images in the B-ultrasonic image testing sets are adjusted to have a resolution of 140×140, the central regions being cropped at a resolution of 120×120, which are input into the trained non-invasive liver fibrosis B-ultrasonic diagnosis model, to obtain the output vectors $\tilde{l}=[\tilde{l}_1, \tilde{l}_2, \tilde{l}_3]$. The category corresponding to the largest value in the vectors $\tilde{l}$ is taken as the liver fibrosis staging result of the B-ultrasonic image.

The invention claimed is:

1. A method for extracting significant texture features of B-ultrasonic images, comprising steps of:
   (1) establishing multi-center ultrasonic image data sets, which comprise B-ultrasonic images of different patients and corresponding liver biopsy results;
   (2) cropping image blocks of three different resolutions from each of the B-ultrasonic images, for data enhancement; partitioning the image blocks into B-ultrasonic image training sets and B-ultrasonic image testing sets at a certain ratio, wherein the image blocks are used as model input data, and the liver biopsy results are used as model label data;
   (3) performing transfer learning on a deep context activation residual network, to obtain a pre-trained liver fibrosis staging model;
   (4) fine-tuning the pre-trained liver fibrosis staging model with the B-ultrasonic image training sets obtained in step (2), to obtain a resulting B-ultrasonic liver fibrosis staging model based on the deep context activation residual network;
   (5) inputting the B-ultrasonic image testing sets obtained in step (2) into the resulting B-ultrasonic liver fibrosis staging model obtained in step (4), to obtain liver fibrosis staging results for the B-ultrasonic images in the B-ultrasonic image testing sets;
   wherein, at step (3), the deep context activation residual network is formed by stacking multiple context activation residual blocks, wherein each of the multiple context activation residual blocks consists of two parts: a residual block and a context activation block, in each of the multiple context activation residual blocks, the residual block is used to extract texture features in each B-ultrasonic image, and each channel for the residual block is responsible for extracting texture information for different features, wherein the context activation block is used to strengthen important texture features in the residual block, while suppressing useless texture features therein, so that the residual block can be used to extract more significant texture features in each B-ultrasonic image, the functional expression of the residual block embedded into the context activation block is as follows:

$$y=f(x)+x=\text{ReLU}(F(BN(W_3 g(W_2 g(W_1 x)))))+x$$

$$g(\cdot)=\text{ReLU}(BN(\cdot))$$

where x and y are the input and output of the residual block, respectively, $BN(\cdot)$ is a batch normalization operation, $\text{ReLU}(\cdot)$ is a rectified linear unit, $F(\cdot)$ is a context activation block, $W_1$ and $W_3$ are both 1×1 convolutions, and $W_2$ is 3×3 convolution.

2. The method according to claim 1, characterized in that the context activation block $F(\cdot)$ mainly comprises three operations: global context aggregation for obtaining global texture information; group normalization for eliminating inconsistent distribution of texture features caused by different samples and enhancing robustness of the pre-trained liver fibrosis staging model; and context activation for learning an importance weight for each channel with global context information, wherein the importance weight describes the importance of the texture feature learned by each channel, wherein the higher a value of the importance weight, the more important the texture feature.

3. The method according to claim 2, characterized in that to simplify, letting $o=F(\cdot)$, wherein the global context aggregation is used to obtain channel characterization vectors $z=[z_1, z_2, \ldots, z_k, \ldots, z_C]$ by global average pooling operation:

$$Z_k = \frac{1}{H \times W} \sum_{i=1}^{W} \sum_{j=1}^{H} o_k(i, j)$$

where W and H are the width and length of a feature map, C represents the number of channels in the feature map, $k \in \{1, 2, \ldots, C\}$, i and j represent the spatial location points with coordinates (i, j) in the feature map,
wherein the group normalization is used to group the channel characterization vectors z per channel dimension, and then normalize feature vectors in each group, to obtain normalized channel characterization vectors $v-[v^1, \ldots, v^i, \ldots, v^G]$, where $v^i$ can be expressed as:

$$v^i = \frac{1}{\sigma^i}(p^i - \mu^i),$$

$$\mu^i = \frac{1}{m}\sum_{n \in S_i} Z_n, \sigma^1 = \sqrt{\frac{1}{m}\sum_{n \in S_i}(Z_n - \mu^1)^2 + \epsilon},$$

where $p^i=[z_{m_i|1}, \ldots, z_{m(i|1)}]$, $$m = \frac{C}{G},$$

G represents the number of groups, $S_i$ represents the channel index set of the i-th group, $\in$ is a small constant for ensuring stable numerical calculation, n represents the channel index, i represents the group index, $\mu^i$ and $\sigma^i$ represent the mean and variance of the i-th group of features respectively, and $v^i$ indicates the normalized i-th group of feature vectors;
wherein the context activation process comprises the step of performing a simple linear transformation on each of the channels and normalizing it to a value between 0 to 1 by a sigmoid function δ, as follows:

$a=\delta(\beta \cdot v+\gamma)$, where β and γ are learnable weights and biases, and · indicates that the corresponding channels are multiplied; wherein the input is readjusted by using the learned texture importance weight, and the output of the context activation block is expressed as $\tilde{o}=o \cdot a$;
embedding the context activation block into the residual block finally, wherein the output of the residual block is re-expressed as:

$y=\text{ReLU}(\tilde{o})+x$.

4. The method according to claim 1, characterized in that in step (4), the fine-tuning the pre-trained liver fibrosis staging model further comprises the steps of:

depending on the B-ultrasonic image training sets obtained in step (2), uniformly adjusting the image blocks with different resolutions to have a resolution of 120×120, which is used as the input for the pre-trained liver fibrosis staging model;

changing the size of the last output layer in the pre-trained liver fibrosis staging model from 1000 to 3, wherein the pathological results of liver biopsy are used as labels; and using a cross-entropy between the output value $\tilde{l}=[\tilde{l}_1, \tilde{l}_2, \tilde{l}_3]$ of the pre-trained liver fibrosis staging model and the label $l=[l_1, l_2, l_3]$ as an objective function, wherein weights in the non-invasive diagnosis model of B-ultrasonic liver fibrosis are fine-tuned by a back-propagation algorithm and a gradient descent method until the value of the objective function is less than a set threshold or a total number of times of training is reached, to obtain the resulting B-ultrasonic liver fibrosis staging model based on the deep context activation residual network.

5. The method according to claim 4, characterized in that the cross-entropy objective function is expressed as follows:

$$\text{Loss} = \min -\frac{1}{m}\sum_{i=1}^{m}\sum_{i=1}^{3} l_i \log(\tilde{l}_i) + \frac{1}{2}\|\theta\|2^2,$$

where m is the total number of training samples, $\tilde{l}_i$ represents an output result of the pre-trained liver fibrosis staging model, $l_i$ is 0 or 1, if and only if the i-th category is 1, and θ represents a training parameter in the pre-trained liver fibrosis staging model.

6. The method according to claim 1, characterized in that the process of obtaining the liver fibrosis staging results of the B-ultrasonic image testing sets in step (5) further comprises the step of:

depending on the B-ultrasonic image testing sets obtained in step (2), uniformly adjusting the image blocks with different resolutions to have a resolution of 140×140, central regions of the image blocks being cropped at a resolution of 120×120, which are input into the resulting B-ultrasonic liver fibrosis staging model to obtain output vectors $\tilde{l}=[\tilde{l}_1, \tilde{l}_2, \tilde{l}_3]$, wherein a category corresponding to the largest value in the output vectors is taken as the final liver fibrosis staging result of each B-ultrasonic image.

* * * * *